United States Patent [19]

Lees et al.

[11] Patent Number: 5,178,864
[45] Date of Patent: Jan. 12, 1993

[54] LIPOPROTEIN REMOVAL BY SOLUBLE ENZYMES

[75] Inventors: Robert S. Lees, Brookline; Robert S. Langer, Jr., Somerville; Regine Labeque, Wakefield; Claudy J. P. Mullon, Framingham, all of Mass.

[73] Assignee: MIT, Cambridge, Mass.

[21] Appl. No.: 567,261

[22] Filed: Aug. 14, 1990

[51] Int. Cl.$^5$ .................... A61K 37/48; A61K 37/54
[52] U.S. Cl. ................................. 424/94.1; 424/520; 424/94.6; 424/542; 514/267; 514/182
[58] Field of Search ............... 514/267, 182; 424/520, 424/94.6, 94.1, 542

[56] References Cited

U.S. PATENT DOCUMENTS

| | | | |
|---|---|---|---|
| 4,079,125 | 3/1978 | Sipos | 424/32 |
| 4,311,788 | 1/1982 | Heuck | 435/7.1 |
| 4,748,161 | 5/1988 | Kimura et al. | 514/182 |
| 4,775,483 | 10/1988 | Mookerjea et al. | 210/670 |
| 4,822,608 | 4/1989 | Benton et al. | 424/539 |
| 4,927,629 | 5/1990 | Bing | 424/94.6 |

OTHER PUBLICATIONS

Heinrikson, et al., J. Biol. Chem. 252, pp. 4913-4921 (1977), USA.
Kramer, et al., J. Biol. Chem. 264, pp. 5768-5775 (1989), USA.
Aggerbeck, et al., J. Biol. Chem. 251, pp. 3823-3830 (1976), USA.
Vadas et al., Lab. Invest., 55, pp. 391-404 (1986), USA.
Mullon et al., Presentation at AIChE annual meeting (Nov. 1989) USA.
Litwin et al., J. of Allergy Clinical Immunology, vol. 75, 1 part 2, 1985, p. 151.
Marmer et al., Chem. Abstracts vol. 90:995809 (1979).

Primary Examiner—Douglas W. Robinson
Assistant Examiner—L. Blaire Lankford
Attorney, Agent, or Firm—Cesari and McKenna

[57] ABSTRACT

A therapeutically effective amount of soluble phospholipase A$_2$ is administered into a subject for lowering the low density lipoproteins ("LDL") in the blood. Phospholipase A$_2$ modifies the plasma LDL by hydrolyzing the phospholipids present in LDL. As a result, the modified LDL is rapidly removed from the bloodstream by the catabolic processes.

12 Claims, No Drawings

LIPOPROTEIN REMOVAL BY SOLUBLE ENZYMES

FIELD OF THE INVENTION

This invention relates generally to a process for treating hypercholesterolemia by reducing cholesterol levels in blood. More particularly, this invention relates to administration of soluble phospholipase $A_2$ into the hypercholesterolemic patient for modification of low density lipoproteins in the blood thereof. The modified low density lipoproteins, being in a readily catabolizable form, are rapidly removed from the bloodstream by the in vivo clearance processes.

BACKGROUND OF THE INVENTION

Coronary heart disease accounts for more deaths annually than any other disease, including all forms of cancer combined. Epidemiologic studies have established that the higher the total plasma cholesterol and low density lipoprotein cholesterol levels, the greater the risk that coronary heart disease will develop.

The low density lipoproteins ("LDL") are those which float in the density range between 1.019 and 1.063 g/ml upon ultracentrifugation. They are composed of about 75% lipid (primarily cholesteryl esters, cholesterol and phospholipids) and 25% protein. Apolipoprotein B, which has a molecular weight of 510,000-dalton, is the principal protein component of LDL.

Under electron microscopy, LDL appear to be globular particles 20-25 nanometers in diameter. Each LDL particle contains approximately 1500 molecules of cholesteryl ester in an oily core that is shielded from aqueous plasma by a hydrophilic coat composed of phospholipids, unesterified cholesterol, and apolipoprotein B. Approximately 65-70% of the total cholesterol is transported in LDL. Thus, removal of LDL leads to a concomitant decrease in cholesterol levels.

Cholesterol and LDL levels are high in many people who have a high dietary intake of cholesterol or fats, and in people with a variety of familial hyperlipidemias including the uncommon, but not rare group who have inherited a genetic defect in the cell surface receptor for LDL.

Total plasma cholesterol and LDL cholesterol levels may be reduced by diet or drugs. However, drug therapy may have potential severe side effects which limit its use. More specifically, drugs that decrease cholesterol synthesis (e.g., lovastatin) have the potential to cause liver injury, cataracts, and fetal abnormalities. Further, many familial hypercholesterolemias (all homozygous types and some heterozygous types) are resistant to diet and drug therapy. Also, drug therapy usually lowers the level of high density lipoproteins ("HDL"), as well as that of LDL, and the former are thought to be protective against atherosclerosis.

Plasmapheresis, the direct removal of the patient's high-cholesterol plasma and replacement with a low-cholesterol fluid, causes only a temporary decrease in HDL levels and is a successful therapy. However, plasmapheresis is extremely expensive. Moreover, this therapy may cause transmission of contagious disease and other complications because of the long-term administration of a large quantity of human plasma products.

Specific removal of LDL only, which obviates the need for replacement with plasma, can be accomplished by using affinity chromatography equipment such as polyanion columns or anti-LDL antibody columns. However, this technique usually requires a two column system; one column removes the LDL from the plasma while the other column is being regenerated. The limited capacity of the adsorbents makes this technique cumbersome and expensive.

LDL in the blood can also be preferentially removed by its reaction with phospholipase C or D, which renders the LDL particles capable of being separated from other blood components by filtration or centrifugation. This method is disclosed in U.S. patent application Ser. No. 241,067 filed Sep. 6, 1988. While this therapy is rather inexpensive, its use is limited to extracorporeal applications.

It has recently been found that LDL modified by the enzyme phospholipase $A_2$ is rapidly cleared from the blood pool by the in vivo catabolic processes. As described in U.S. patent application Ser. No. 101,262 filed Sep. 25, 1987, reactors containing immobilized phospholipase $A_2$ are used for extracorporeal or intracorporeal treatment to lower plasma LDL levels. One major drawback about this approach is that it requires that immobilized phospholipase $A_2$ be used. It thus imposes a great restraint on the technical design of therapeutic systems based on the concept of in vivo clearance of modified LDL. More specifically, an immobilized enzyme-containing reactor has to be connected to the patient, either extracorporeally or intracorporeally, during treatment. Also, the immobilization process often significantly reduces the enzyme activities.

SUMMARY OF THE INVENTION

Accordingly, it is an object of this invention to provide a simple and low-cost method for lowering plasma cholesterol levels without resorting to the cumbersome or expensive techniques involving plasma exchange, affinity chromatography, or immobilized enzyme-containing reactors.

It is another object of this invention to provide a method for decreasing the concentration of plasma cholesterol by its removal from the blood pool, thereby avoiding the severe side effects known to be associated with hypocholesterolemic drugs which reduce cholesterol by inhibiting the synthesis thereof.

It is a further object of this invention to provide a method for decreasing the concentration of plasma cholesterol by its removal from the blood pool and is thus effective in treating both homozygous and heterozygous patients with familial hypercholesterolemia.

It is yet another object of this invention to provide a method for decreasing the concentration of plasma cholesterol by removing LDL while retaining HDL which are thought to provide protection against atherosclerosis and whose presence in the blood may be desirable.

These and other objects will become more apparent as the description herein proceeds.

In accordance with the present invention, soluble phospholipase $A_2$ in a therapeutically effective amount is administered by a suitable method. In one embodiment, the enzyme is dissolved in a saline solution and slowly perfused intravenously into the bloodstream of the subject.

This treatment, a drug therapy in essence, greatly facilitates the catabolism of plasma LDL. As a result, the LDL and cholesterol levels in the subject's blood decrease substantially in a matter hours.

DETAILED DESCRIPTION OF THE INVENTION

Phospholipases $A_2$ (phosphatide 2-acylhydrolases, EC3.1.1.4) are a diverse family of enzymes that hydrolyze the sn-2 fatty acyl ester bond of phosphoglycerides, producing free fatty acids and lysophospholipids. Phospholipases $A_2$ are abundant in pancreatic juice and in the venoms of snakes and arthropods, where they serve degradative functions. However, they also occur in trace amounts in every cell type studied so far, where they play crucial roles in normal cellular functions by participating in the metabolism and turnover of phospholipids.

To date more than 30 complete amino acid sequences have been reported for phospholipases $A_2$ from various sources. Generally speaking, these enzymes are small, having about 120 amino acid residues in a polypeptide chain cross-linked with 4 to 7 disulfide bonds. All phospholipases $A_2$ isolated from mammalian tissues and venoms of snakes show remarkable homology and may be considered together in terms of their shared chemical similarities. On the other hand, the honeybee venom enzyme differs materially in its structure as compared with other phospholipases $A_2$. Thus, all phospholipases $A_2$ sequenced so far can be divided into two categories, with the bee venom phospholipase $A_2$ belonging to one category and the other enzymes from various vertebrate sources forming a large second category.

The second large homologous category of enzymes may be divided further into two structural classes based on their amino acid sequences [Heinrikson et al., *J. Biol. Chem.*, 252:4913 (1977)]. Group I enzymes, defined by a disulfide bridge between residues 11 and 69 (based on the numbering system of the rattlesnake [*Crotalus atrox*] enzyme here and also below), include those from mammalian pancreas and the venoms of the snake families of cobras and sea snakes. Group II enzymes, which possess a carboxy-terminal sequence extension linked by a disulfide to a cysteine near the presumed active site, include phospholipases $A_2$ from mammalian platelets and the venoms of the viper (both pit viper and old world viper) and rattlesnake families.

The honeybee venom phospholipase $A_2$ is quite distinct from the group I and II enzymes structurally. Although similar in size, it has fewer disulfide bonds and it is difficult to find much sequence homology with other phospholipases $A_2$. However, the honeybee venom enzyme has the sequence Cys-Cys-Arg-Thr-His-Asp-Met-Cys which is identical with a segment in the active site region of the group I phospholipases $A_2$ comprising residues 43-50.

It was reported by Aggerbeck et al., *J. Biol. Chem.*, 251:3823 (1976) that phospholipase $A_2$ from *C. atrox* is able to modify LDL by hydrolyzing the phospholipids present therein. In our recent studies on LDL metabolism in rabbits, it was found that LDL modified by phospholipase $A_2$ from honeybee venom is rapidly cleared from the bloodstream. In one experiment, 55% of the intravenously administered phospholipase $A_2$-modified LDL was found to be removed from the blood pool in 10 minutes. By contrast, a 15% decrease in the level of injected native, unmodified LDL was observed one hour after the injection. The biodistribution of native and modified LDL in both normal and hypercholesterolemic rabbits indicates that the modified LDL are removed mainly by the liver.

The discovery that modified LDL are subject to rapid metabolism suggested to us a novel therapeutic approach for treating hypercholesterolemia. More particularly, the total plasma LDL levels can be lowered by simply circulating soluble phospholipase $A_2$ in the bloodstream to modify LDL therein. The enzymatically modified LDL are then rapidly removed by the in vivo catabolic processes, thereby resulting in decrease of both cholesterol and LDL levels of the patient.

Phospholipases $A_2$ are known to catalyze lysis of some cells, e.g., erythrocytes, presumably by hydrolyzing the phospholipids in the cellular membranes. Based on this concern, immobilized phospholipase $A_2$ was first used by us to modify plasma LDL so that the enzyme could not gain access to tissues or organs of the subject to cause any harmful effects.

In the present invention, we have nonetheless demonstrated that administration of soluble phospholipase $A_2$ into the bloodstream, if performed in a proper manner, can substantially lower the plasma cholesterol levels in a few hours without causing any significant or irreversible adverse side effects to the recipient.

Purified phospholipases $A_2$ from various sources are commercially available. Ideally, human phospholipase $A_2$ is preferred in treating hypercholesterolemic patients as it is most compatible with the human immune system. Human phospholipase $A_2$ can be purified from platelets (a group II enzyme) by the method described by Apitz-Castro et al., *Biochem. Biophys. Res. Comm.*, 91:63 (1979). Since the gene of the human phospholipase $A_2$ from platelets has recently been cloned by Kramer et al., *J. Biol. Chem.*, 264:5768 (1988), production of this enzyme in large quantities now seems feasible.

In the embodiments described herein, soluble phospholipases $A_2$ from two sources, i.e., bee venom and rattlesnake (*C. atrox*) venom, were used. Each enzyme represents, respectively, one of the two categories of the phospholipase $A_2$ families. The bee venom enzyme, as described hereinbefore, is structurally distinct from phospholipases $A_2$ from mammalian and reptile sources. While the latter enzymes can be further divided into two groups, the enzymes in both groups are highly homologous in sequence. For example, comparing the sequences of bovine pancreas phospholipase $A_2$ (a group I enzyme) and *C. atrox* phospholipase $A_2$ (a group II enzyme), their homologous segments range from 7 to 20 amino acids in length and together comprise 62% of the minimal sequence. Crystallographic studies further show that these two enzymes are also similar in their three-dimensional structures. Thus, the *C. atrox* enzyme is representative of all the phospholipases $A_2$, with the single exception of the bee venom enzyme, which have been studied so far.

Results from our experiments with rabbits show that phospholipase $A_2$ from either bee venom or *C. atrox*, after being injected into the bloodstream, is capable of lowering cholesterol levels. More specifically, in one embodiment of the present invention, a therapeutically effective amount of phospholipase $A_2$ from either source (e.g., 5000 units of bee venom enzyme or 500 units of *C. atrox* enzyme, see Tables 1 and 2) was first dissolved in a pre-determined volume of saline solution. The resultant phospholipase $A_2$ solution was gradually administered into the bloodstream of a rabbit over a period of 90 minutes. As a result of this treatment, a drop of 26-43% (33% average) in total plasma cholesterol was observed at the end of the administration. The decrease in cholesterol levels continued afterwards for a period of time. A total decrease of 33-60% (45% average) in total cholesterol levels was observed 3 hours after the administration was completed, or 4.5 hours after the administration was started.

Significant variance respecting the cholesterol decrease in these experiments was expected for numerous reasons.

TABLE 1

Cholesterol Measurements in Hypercholesterolemic Rabbits upon Infusion of Phospholipase $A_2$ (PLA$_2$)

|  | Rabbit 1 | Rabbit 2 | Rabbit 3 |
|---|---|---|---|
| Activity of PLA$_2$ injected | 1000 units (bee venom) | 5000 units (bee venom) | 500 units (C. atrox) |
| Total cholesterol (mg/dl) |  |  |  |
| Initial | 898 | 589 | 190 |
| 90 minutes | 785 (−13%)* | 436 (−26%) | 135 (−29%) |
| 4.5 hours | — | 392 (−33%) | 111 (−42%) |
| Total triglycerides (mg/dl) |  |  |  |
| Initial | 115 | 162 | 77 |
| 90 minutes | 60 (−48%) | 100 (−38%) | 100 (+30%) |
| 4.5 hours | — | 150 (−7%) | — |

*(percentage change)

TABLE 2

Lipoproteins/Cholesterol Determination upon Slow Infusion of 500 units C. atrox Venom

|  | Total Cholesterol | HDL | LDL | VLDL |
|---|---|---|---|---|
| Initial | 283 | 16 | 171 | 96 |
| 90 min. | 160 | 32 | 102 | 26 |
| % change | −43% | +100% | −40% | −73% |
| 4.5 hours | 114 | 37 | 51 | 26 |
| % change | −60% | +131% | −70% | −73% |

First, the initial cholesterol levels in the rabbits differed greatly, i.e., ranging from 190 to 898 mg/dl. Also, phospholipases $A_2$ from different sources and in different amounts were used. Nonetheless, our results clearly demonstrate the effect of phospholipase $A_2$ in substantially lowering plasma cholesterol in a matter of hours.

By contrast, the level of plasma triglyceride was found to increase in one experiment and decrease in another at the end of the 90-minute intravenous perfusion. In any event, it was shown in a third experiment that the triglyceride level measured 3 hours after the administration was completed was essentially the same as the initial level. These results are shown in Table 1.

Our experimental results also suggest that the C. atrox phospholipase $A_2$ is more effective for lowering plasma cholesterol than the bee venom enzyme. As shown in Table 1, ten times the amount of the enzyme from bee venom was required, as compared with the amount of C. atrox venom, in order to achieve a comparable decrease in cholesterol levels.

In one experiment, changes in cholesterol content of different lipoproteins were measured before and after administration of phospholipase $A_2$. As shown in Table 2, three hours after the administration of phospholipase $A_2$ was completed, there was a decrease of 169 mg/dl (from 283 mg/dl to 114 mg/dl) in total cholesterol level. This decrease was accompanied by a corresponding decrease of 120 mg/dl (from 171 mg/dl to 51 mg/dl) in LDL cholesterol. The concomitant decreases are in agreement with the underlying principle of this invention. That is, rapid catabolism of LDL modified by phospholipase $A_2$ effects a decrease in plasma cholesterol, since about 65-70% of the total cholesterol in the bloodstream is transported in LDL. In this context, it should be pointed out that modification of plasma LDL after intravenous perfusion of phospholipase $A_2$ into the subject was confirmed both directly by monitoring the hydrolysis of phospholipids in LDL and indirectly by monitoring chromatographically the increase in lipoprotein mobility on paper.

As also shown in Table 2, the pattern of changes in cholesterol content of very low density lipoproteins ("VLDL") essentially follow that of LDL. The cholesterol content of HDL, on the other hand, was found not to decrease after administration of phospholipase $A_2$ into the blood pool. Presumably, phospholipase $A_2$ preferentially reacts with phospholipids in LDL (and VLDL) over those in HDL. A similar phenomenon has also been observed with another enzyme which reacts with phospholipids, i.e., phospholipase C. As mentioned hereinbefore, HDL are thought to be protective against atherosclerosis. Thus, the preference of phospholipase $A_2$ to attack phospholipids present in LDL over those in HDL provides an additional advantage in using this enzyme as a drug for treatment of hypercholesterolemia.

Phospholipases $A_2$ are known to cause damage to some cells, presumably by hydrolyzing the phospholipids in the cellular membranes. As a criterion of the extent of damage the rabbits might have suffered by the phospholipase $A_2$ treatment as described above, hemolysis assay was performed at the end of each experiment. It was found that only 10 to 20% of the red blood cells lyzed in all experiments, as indicated by the ratio of the resultant free hemoglobin content to the initial total hemoglobin content. By contrast, 80-90% of the phospholipids in lipoproteins were hydrolyzed at the end of the perfusion with phospholipase $A_2$. Apparently, plasma lipoproteins, including LDL, are more vulnerable than red blood cells to the attack by phospholipase $A_2$. In any event, all the rabbits which underwent the phospholipase $A_2$ treatment not only survived the procedure, but also remained healthy for more than two months before they were sacrificed for other experimental purposes.

Therefore, we have clearly demonstrated the efficacy of the present invention, namely, administration of phospholipase $A_2$ in a proper manner into the bloodstream of a subject, thereby to achieve a substantial reduction of plasma cholesterol in a few hours without causing any significant or irreversible effects to the subject.

The dosage of phospholipase $A_2$ to be administered will, of course, depend upon the severity of the condition being treated, the route of administration chosen, the body weight of the subject, the specific activity of the phospholipase $A_2$ and the sources of the enzyme. As an example of dosage effect, it is shown in Table 1 that when the amount of bee venom phospholipase $A_2$ was increased from 1,000 units to 5,000 units, the decrease in the total cholesterol doubled from 13% to 26%. Also, as mentioned hereinbefore, the C. atrox phospholipase $A_2$ is much more effective than the bee venom enzyme in lowering plasma cholesterol levels. Thus, a lower dosage should be used for the C. atrox enzyme. In practice, the dosage to be administered should ultimately be decided by the attending professional personnel. The dosage of phospholipase $A_2$ which lowers LDL levels without causing significant or irreversible side effects is referred to herein as a "therapeutically effective amount."

The therapeutically effective amount of phospholipase $A_2$ may be administered by any route appropriate to the condition being treated. Preferably the enzyme is injected into the bloodstream of the subject being treated. It will be readily appreciated by those skilled in the art that the preferred route, such as intravenous, subcutaneous, intramuscular, intraperitoneal, bronchial, nasal, oral, etc., will vary with the condition being treated and the biochemical property of the enzyme being used.

While it is possible for phospholipase $A_2$ to be administered as the pure or substantially pure protein, it is preferable to present it as a pharmaceutical formulation or preparation.

The formulations of the present invention, both for human and for veterinary use, comprise purified phospholipase $A_2$ together with one or more pharmaceutically acceptable carriers therefor and optionally other therapeutic ingredients. The carriers must be "acceptable" in the sense of being compatible with the other ingredients of the formulation and not deleterious to the recipient thereof. Desirably, the formulation should not include oxidizing agents and other substances with which proteins are known to be incompatible. Rather, it is preferable that the carriers be capable of stabilizing the enzyme so that its shelf life can be prolonged.

The formulations may conveniently be presented in unit dosage form and may be prepared by any of the processes well known in the art of pharmacy. All processes include the step of bringing purified phospholipase $A_2$ into association with the carrier which constitutes one or more accessory ingredients.

In general, the formulations for tablets or powders are prepared by uniformly and intimately blending lyophilyzed phospholipase $A_2$ with finely divided solid carriers, and then, if necessary as in the case of tablets, shaping the product into the desired shape and size. These solid formulations are suitable for oral ingestion.

Formulations to be used for parenteral administration, on the other hand, conveniently comprise sterile aqueous solutions of phospholipase $A_2$. Preferably, the solutions are isotonic with the blood of the recipient. Such formulations may be conveniently prepared by dissolving solid phospholipase $A_2$ in water to produce an aqueous solution, and subsequently rendering the solution sterile. The formulations may be presented in unit or multi-dose containers such as sealed ampoules or vials.

We have described herein specific embodiments of the present invention. It will be apparent, however, that variations and modifications may be made to the invention, with the attainment of some or all of the advantages of the invention.

For example, the phospholipases $A_2$ which can be used in the present invention are not limited to the enzymes which have been isolated and studied so far. However, it is preferable that they be soluble in blood and require no cofactors other than those present therein.

Also, it is possible to use hybrid proteins, synthesized by recombinant DNA technology, which are not only capable of hydrolyzing the sn-2 acyl ester bond of phospholipids, but also possess some other desirable property. By way of example, a hybrid protein which is not only able to modify LDL but is also resistant to digestion by gastric proteases could be conveniently and effectively administered via the oral route for treatment of hypercholesterolemia.

Another improvement of this invention comprises the use of polyethyleneglycol-phospholipase $A_2$ and modifications thereof. Covalent attachment of polyethylene glycol to an enzyme has been found to block access to sites on the surface of the enzyme, thereby inhibiting clearance from the bloodstream, attack by proteases and binding of antibodies, and processing by antigen-presenting cells required for generation of an immune response. As a result, the administered enzyme is rendered less antigenic and its circulating life prolonged [Hershfield et al., *N. Engl. J. Med.*, 316:589 (1987); Ho et al., *Drug Metab. Dispos.*, 14:349 (1986); Chua et al., *Annals of Internal Med.*, 109:114 (1988)].

Alternatively, it may be desirable to administer phospholipase $A_2$ which is conjugated to an antibody directed at LDL for specific targeting of the enzyme to LDL. It is well known in the art that increase of drug effectiveness or diminution of drug side effects can be achieved by chemical coupling of drugs to carriers such as antibodies or other soluble binding proteins with preferential affinity toward the target molecules or cells [Hurwitz, et al., *J. Med. Chem.*, 28:137 (1985); Till et al., *Science*, 242:1166 (1988)].

The following examples are provided to aid in the understanding of the present invention, the true scope of which is set forth in the appended claims. It is understood that modifications can be made in the procedures set forth, without departing from the spirit of the invention.

EXAMPLE I

Bee venom phospholipase $A_2$ (1,000 or 5,000 units) was dissolved in about 5 ml sterile saline to form an enzyme solution with a concentration of 200 units per ml. The bee venom phospholipase $A_2$ was purchased from Sigma, St. Louis, Mo. The enzyme activity was determined at pH 8.9 at 25° C. using soybean L-alpha-phosphatidyl choline as substrate.

The enzyme solution was gradually perfused intravenously over a 90 minute period into a New Zealand white rabbit (Hazelton, Denver, Pa.) which had been fed a 1% cholesterol diet (Purina, Framingham, Mass.) for one to three weeks. The perfusions were performed through the marginal vein with a Minicath infusion set, 23G (Deseret Med. Inc., Sandy, Ut.)

At three time points, i.e., zero time, 90 minutes and 4.5 hours after the perfusion was initiated, blood samples were taken from the ear artery with a Minicath infusion set, 21G for measurements of total cholesterol and triglyceride levels, as well as hemolysis.

Total cholesterol measurement was performed using the kit Choles-Cinet, which comprised a mixture of cholesterol ester hydrolase, cholesterol oxidase, horseradish peroxidase, hydroxybenzoate sodium salt, 4-aminoantipyrine, and sodium azide in phosphate buffer. The kit was purchased from Sclavo Diagnostics, Wayne, N.J. The cholesterol was measured by a colorimetric method on an automated system as described by Henry, et al., *Clinical Chemistry; Principles and Techniques,* Harper and Rows eds, 1440, New York (1975).

Total triglyceride measurement was obtained with the A-gent kit from Abbott, North Chicago, Ill. A-gent is a mixture of NADH, phosphoenolpyruvate, ATP disodium salt, $MgSO_4$; Tris buffer, succinic anhydride, lipase, lactic dehydrogenase, pyruvate kinase, and glycerol. The triglyceride was hydrolyzed by a microbial lipase to free glycerol and free fatty acids. The liberated free glycerol was then determined by disappearance of NADH at 340 nm on an automated system, Biochromatic Analyzer 100, from Abbott. Bucolo et al., *Clinical Chemistry,* 19:476 (1975); Sampson et al., *Clinical Chemistry,* 21:1983 (1975).

Total cholesterol and triglyceride levels measured at different time points are shown in Table 1, the two columns under the headings "Rabbit 1" and "Rabbit 2".

Hemolysis was measured spectrophotometrically according to the method reported by Kahn et al., *Ann. Clin. Lab. Science.* 11:126 (1981). Free hemoglobin after the intravenous perfusion was found to be 10–20% the initial value for total hemoglobin.

EXAMPLE II

*C. atrox* phospholipase $A_2$ (500 units) was dissolved in about 5 ml sterile saline to form an enzyme solution with a concentration of about 80 units per ml. *C. atrox* phospholipase $A_2$ was purified from lyophilized *C. atrox* (Western diamondback rattlesnake) venom purchased from Miami Serpentarium (Salt Lake City, Ut.) by a procedure described by Hachimori et al., *Biochemistry,* 10:1971 (1975). The enzyme activity was determined at pH 8.9 at 25° C. using soybean L-alpha-phosphatidyl choline as substrate.

The same procedures, as described in Example I, were followed.

Total cholesterol and triglyceride levels measured at different time points are shown in Table 1, the right column under the heading "Rabbit 3".

Free hemoglobin, after the phospholipase $A_2$ treatment was found to be 10–20% the initial value for total hemoglobin.

EXAMPLE III

*C. atrox* phospholipase $A_2$ (500 units) was dissolved in about 5 ml sterile saline to form an enzyme solution with a concentration of about 80 units per ml. Blood samples were take at different time points. All procedures were performed following those described in Examples I and II.

Cholesterol contents of different plasma lipoproteins were determined using the kit Choles-Cinet from Sclavo Diagnostics, Wayne, N.J. as follows.

Subsequent to plasma precipitation with manganese chloride and heparin, HDL cholesterol which did not precipitate was measured in the supernatant. The values for LDL cholesterol were calculated as a difference between total cholesterol and HDL cholesterol plus 1/5 of triglyceride (estimated value of VLDL).

In another case, LDL cholesterol levels were determined after centrifugation at 42,000 rpm for 22 hours at a 1.006 density to remove triglyceride and VLDL. After removal of VLDL and triglyceride, total cholesterol and HDL cholesterol were measured. LDL cholesterol was calculated as the difference between total cholesterol and HDL cholesterol.

Cholesterol contents of LDL, HDL and VLDL measured at different time points are shown in Table 2.

Hemolysis assay was also performed. As in Examples I and II, free hemoglobin after perfusion was 10–20% the initial value for total hemoglobin.

What is claimed is:

1. A process for lowering the level of low density lipoproteins ("LDL") in a subject's blood, which process comprises
administering a therapeutically effective amount of the enzyme phospholipase $A_2$ into the subject to hydrolyze the sn-2 fatty acyl ester bond of phosphoglycerides of the LDL in such a form that they are subject to rapid removal by the in vivo catabolic processes.

2. The process as described in claim 1 wherein the phospholipase $A_2$ is purified from arthropod venom.

3. The process as described in claim 2 wherein the phospholipase $A_2$ is purified from bee venom.

4. The process as described in claim 1 wherein the phospholipase $A_2$ is purified from the group consisting of cobra venom, sea snake venom, rattlesnake venom, pit viper venom, old world viper venom, pancreas, and platelets.

5. The process as described in claim 4 wherein the phospholipase $A_2$ is purified from rattlesnake venom.

6. The process as described in claim 1 wherein the enzyme is coupled to an antibody directed at LDL prior to its administration into the subject.

7. The process as described in claim 1 wherein the enzyme is covalently attached to polyethyleneglycol prior to its administration into the subject.

8. The process as described in claim 1 wherein the enzyme is a hybrid protein resistant to gastric proteolysis.

9. The process as described in claim 1 wherein the administration is performed by a method selected from the group consisting of intravenous injection, subcutaneous injection, intramuscular injection, intraperitoneal injection, nasal insufflation, and oral ingestion.

10. The process as described in claim 1 wherein the administration is performed by intravenous perfusion of a saline solution in which the enzyme is dissolved.

11. The process as described in claim 1 wherein the enzyme is contained in a pharmaceutically acceptable vehicle prior to its administration into the subject.

12. A process for lowering the level of low density lipoproteins ("LDL") in blood, which process comprises exposing the LDL to the enzyme phospholipase $A_2$, thereby hydrolyzing the sn-2 fatty acyl ester bond of phosphoglycerides of the LDL in such a form that they are subject to rapid removal by the in vivo catabolic processes.

* * * * *